United States Patent
Dall'Oglio

(10) Patent No.: US 10,932,998 B2
(45) Date of Patent: Mar. 2, 2021

(54) HYDROGEN PEROXIDE-BASED OXIDIZING COMPOSITION FOR USE IN COMBINATION WITH HAIR BLEACHES OR WITH LIGHTENING OR SUPER-LIGHTENING HAIR DYES

(71) Applicant: Mara Dall'Oglio, Bagnolo S. Vito (IT)

(72) Inventor: Mara Dall'Oglio, Bagnolo S. Vito (IT)

( * ) Notice: Subject to any disclaimer, the term of this patent is extended or adjusted under 35 U.S.C. 154(b) by 0 days.

(21) Appl. No.: 16/351,593

(22) Filed: Mar. 13, 2019

(65) Prior Publication Data
US 2019/0282469 A1 Sep. 19, 2019

(30) Foreign Application Priority Data
Mar. 15, 2018 (IT) .................. 102018000003607

(51) Int. Cl.
| | |
|---|---|
| *A61K 8/22* | (2006.01) |
| *A61K 8/49* | (2006.01) |
| *A61K 8/23* | (2006.01) |
| *A61K 8/25* | (2006.01) |
| *A61Q 5/06* | (2006.01) |
| *A61Q 5/08* | (2006.01) |
| *A61Q 5/10* | (2006.01) |

(52) U.S. Cl.
CPC .................. *A61K 8/22* (2013.01); *A61K 8/23* (2013.01); *A61K 8/25* (2013.01); *A61K 8/49* (2013.01); *A61K 8/498* (2013.01); *A61K 8/4973* (2013.01); *A61Q 5/065* (2013.01); *A61Q 5/08* (2013.01); *A61Q 5/10* (2013.01); *A61K 2800/43* (2013.01); *A61K 2800/592* (2013.01); *A61K 2800/88* (2013.01)

(58) Field of Classification Search
None
See application file for complete search history.

(56) References Cited

U.S. PATENT DOCUMENTS

| | | | | |
|---|---|---|---|---|
| 5,846,570 A | * | 12/1998 | Barrow | ................ A61K 8/042 424/616 |
| 2017/0079901 A1 | * | 3/2017 | Hippe | ................ A45D 7/02 |

FOREIGN PATENT DOCUMENTS

| | | |
|---|---|---|
| WO | 2002074270 A1 | 9/2002 |
| WO | 2010054981 A2 | 5/2010 |

OTHER PUBLICATIONS

Search Report if priority application IT2018000003607 of Nov. 13, 2018.

* cited by examiner

*Primary Examiner* — Sin J Lee
(74) *Attorney, Agent, or Firm* — Silvia Salvadori, P.C.; Silvia Salvadori

(57) ABSTRACT

The present invention relates to a fluid/creamy pigmented hydrogen peroxide-based oxidising composition, to be used in combination with persulfates-based hair bleaches or with dyes, lightening, super-lightening products. The composition of the semi-finished product includes hydrogen peroxide in various titles in proportions from 1% to 12% by weight, plus other substances in addition to a first dye which provides the semi-finished product with a yellow/green colour at an acid pH. By combining the oxidising composition (first product) with bleaching products of various nature/lightening dyes (second product) in an emulsion, the pH of the emulsion becomes strongly alkaline, from the initial 2-3 it may increase up to 11.5. In this pH transition from acid to alkaline, the oxidising emulsion changes its colour from yellow/green to blue. In the pH passage of the emulsion from acid values to alkaline values, the blue that has formed is chromatically active against the orange and red reflections, present on the hair as residual colours due to previous treatments.

14 Claims, No Drawings

HYDROGEN PEROXIDE-BASED OXIDIZING COMPOSITION FOR USE IN COMBINATION WITH HAIR BLEACHES OR WITH LIGHTENING OR SUPER-LIGHTENING HAIR DYES

This Non-Provisional Application claims priority to and the benefit of Italian Application No 102018000003607 filed on Mar. 15, 2018 the content of which is incorporated herein by reference in its entireties.

DESCRIPTION

Field of Application

The present invention relates to products for hair bleaching and/or dyeing.

In particular, the present invention relates to a pigmented hydrogen peroxide-based oxidising composition for use in hair bleaching or hair dyeing by means of oxidation dyes, lightening, super-lightening products.

The present invention further relates to a product for use in hair bleaching in the form of a kit comprising, in separate containers, a hydrogen peroxide-based (peroxide) oxidising composition and a bleaching composition containing a boosting oxidising agent and a pH-adjusting agent or an alkalizing agent.

The present invention also relates to a product for hair bleaching in the form of a kit comprising, in separate containers, hydrogen peroxide-based (peroxide) oxidising composition and an oxidation dye, in particular, but non-exclusively, of the lightening or super-lightening type comprising an oxidation precursor and a coupler.

Prior Art

Hair bleaching is a well-known process in the cosmetic field. Bleaching (lightening) is the result obtained by the application of an emulsion formed by a hydrogen peroxide-based oxidising agent having acid pH with ammonium, potassium and sodium persulfates that develop oxygen in an alkaline environment through an oxidation-reduction reaction. The lightening action by the oxidising agent is progressive over time, therefore depending on the desired result the application time may vary from 10 to 60 minutes. The oxidising agent is typically a hydrogen peroxide solution in concentrations varying from 3 to 12% by weight. The reaction between hydrogen peroxide and ammonium, potassium and sodium persulfates-based bleaches develops oxygen that attacks and disrupts the melaninic granules which are responsible for hair dyeing. In this lightening treatment, even after washing the hair with removal/elimination of colour residues of melaninic origin, unaesthetic orange/reddish reflections remain on the hair. Usually, the alkaline emulsion is the result of the presence of alkalizing agents, such as metasilicate sodium/metasilicates of various types. The hydrogen peroxide in an alkaline environment is destabilized, thus releasing oxygen that attacks the melanin pigments present on the hair.

To obtain the lightening effect on the hair, the hydrogen peroxide (oxidising) interacts with persulfate salts, (sodium, potassium, ammonium or mixtures thereof), as well as with carbonate salts and/or silicates as an alkalinity source.

The aforementioned bleaching products may be provided both for professional use and in the form of a kit for domestic use.

The hair may be not uniformly bleached due to the different oxidative decomposition rates of the various melaninic pigments present in the hair fibre by the above oxidising components. Especially in the case of bleaching of darker hair with a high content of melaninic pigments, residues with colour shades towards unaesthetic tones, typically in the form of yellowish, orange and/or reddish reflections, remain thereon.

These reflections are generally undesirable and unaesthetic. To avoid this drawback, it is necessary to contrast the colour of the above reflections with a complementary and antagonistic colour according to the theory based on which the colours give a chromatic sum: yellow+blue=green, red+blue=purple. This operation is known to the skilled persons as "matting", a result obtained by using a contrasting colour.

Hair bleaching compositions already containing compatible "matting" agents to counteract the variation in colour deriving from the bleaching residues are also known in the art. Said compositions may be directly used on the hair in a single-phase application, thus obtaining both bleaching and counteraction of the reflections resulting from bleaching (Bleach & Colour).

For instance, WO 2010054981 patent application describes a composition containing bleaching-activating compounds based on some pyridinium cationic derivatives in combination with a dyeing agent balancing the colour of the bleaching residues. This composition is said to reduce the damage to the hair which usually follow the bleaching oxidative process while counteracting the colour of the bleaching residues by means of a chromatic combination with the dyeing agent. In an embodiment, the dyeing agent comprises a combination of at least one direct blue dye, among which 3,3',3",4,5,5',5",6-ottabromophenol-sulfoneftalein (tetrabromophenol blue) and at least one direct red dye, among which Acid Red 52. The above composition is used in combination with a hydrogen peroxide-based oxidising composition and the resulting product is applied onto the hair for a one-phase bleaching.

However, the above compositions are not satisfactory since the pigments used tend to form aggregates with the residual component colours present on the hair. Furthermore, the above compositions find application limited to hair bleaching in the combination between an oxidising cream added to a bleaching powder.

The main object of the present invention is thus to provide the user (hairdresser or final consumer) with a polyfunctional product that may be used in combination with different lightening compositions (for instance persulfates) in the different hair bleaching and/or dyeing-lightening alternatives which is simpler, cheaper and more functional than the prior art treatments and, at the same time, effective in eliminating undesired/unaesthetic reddish-orange reflections. Thus, the object of the present invention is to make an easy and effective method for counteracting the undesired chromatic reflections in the context of hair bleaching with dyes, lightening, super-lightening products available to the professional/final consumer.

SUMMARY OF THE INVENTION

The above objects are primarily achieved by a peroxide-based oxidising composition for use in hair bleaching or hair dyeing, the composition comprising, in a cosmetically acceptable carrier, hydrogen peroxide in proportions from 1% to 12% by weight on the weight of the composition, at least a first dye which per se assumes an azure or blue colour at a pH higher than 7, preferably at a pH between 8 and 11.5, and optionally at least one second dye which per se assumes a red colour at a pH higher than 7, preferably at a pH between 8 and 11.5.

The above objects are achieved by the present invention also by means of a product for hair bleaching in the form of a kit comprising in separate containers:

a) a peroxide-based oxidising composition as above defined, b) a bleaching composition containing an oxidising agent other than hydrogen peroxide and at least one pH-adjusting agent able to change the pH to a value higher than 7, preferably a pH between 8 and 11.5, when the oxidising composition is mixed with the bleaching composition.

The above objects are also achieved by a product for hair bleaching in the form of a kit comprising in separate containers:

a) a peroxide-based oxidising composition as above defined, b) an oxidation dye comprising an oxidation precursor and a coupler.

According to a preferred embodiment, the peroxide-based oxidising composition comprises a first dye which per se assumes an azure or blue colour at a pH higher than 7 and a second dye which per se assumes a red colour at a pH higher than 7.

Thus, the present invention may be applied not only in the hair bleaching field but also in the hair dyeing field by means of oxidation dyes, in particular lightening or super-lightening dyes still in order to leave the hair in a natural appearance which is not spoiled by unaesthetic orange reflections.

In this context, the pigmented hydrogen peroxide-based oxidising composition may be provided per se as a professional product packaged for example in 500- or 1000-ml bottles. Alternatively, the package may contain two separate containers, one containing the pigmented hydrogen peroxide-based oxidising composition and the other one containing the bleaching or dyeing composition in the different forms or dyes, lightening and super-lightening products.

Further features and advantages of the present invention will become more apparent from the following detailed description and non-limiting examples.

DETAILED DESCRIPTION

In the present invention, the at least one oxidising agent of the bleaching composition preferably consists of persulfates, in particular monopersulfates such as, for instance, potassium persulfate, sodium persulfate, ammonium persulfate or mixtures thereof.

According to another particularly preferred embodiment, the oxidising agent consists of a mixture of potassium persulfate and ammonium persulfate.

The at least one oxidising agent in the bleaching composition is used in an amount enough to lighten/bleach the hair in combination with the peroxide-based oxidising composition (hydrogen peroxide).

The bleaching composition may further contain at least one pH-adjusting agent which is per se known in the cosmetic treatment of keratin fibres. Said pH-adjusting agent is of the type able to provide alkalinity and may be preferably selected from the group consisting of sodium metasilicate, silicate compounds and carbonate compounds in mixtures in the physical state of powder and/or based on monoethanolamine or ammonium hydroxide in the creamy or liquid formulations of the dyes/lightening/super-lightening products. The pH-adjusting agent in the bleaching composition is present in an amount able to adjust pH from 8 to 11.5, when the bleaching composition is mixed with the peroxide-based oxidising composition to obtain an emulsion.

For instance, the amount of pH-adjusting agent may be comprised between 1% and 40% by weight on the overall weight of the bleaching composition.

The bleaching composition may be in any form useful for forming an emulsion with the hydrogen peroxide-based oxidising composition at the time of use, for instance it may be in the form of powder, cream, paste or bleaching oil.

Depending on the chosen form, the bleaching composition may contain further ingredients conventionally used in the cosmetic field such as:

rheology-modifying agents (thickeners), such as for instance cationic, anionic or non-ionic amphoteric polymers, cellulose-based thickeners (for instance hydroxyethyl cellulose, hydroxypropyl cellulose, carboxymethylcellulose, cellulose ether cationic derivatives, quaternized cellulose derivatives), guar gum and derivatives thereof, xanthan gum, acrylic acid cross-linked homopolymers, etc., drying agents, such as silica to prevent moisture from reacting with the oxidising agent (for example persulfates) prior to mixing the activator component with the peroxide-based developer component, surfactants, such as sodium lauryl sulfate and sodium stearate, excipients, such as magnesium carbonate.

In the present invention, the peroxide-based oxidising composition comprises hydrogen peroxide in proportions from 1% to 12% by weight and a cosmetically acceptable carrier.

The cosmetically acceptable carrier is preferably water.

Preferably, the oxidising composition comprises an aqueous solution containing hydrogen peroxide in proportions from 1% to 12% by weight. For instance, a 12% solution corresponds to a oxidising cream having 40 by volume of hydrogen peroxide so that a litre of 40 by volume of hydrogen peroxide is able to release 40 litres of gaseous oxygen under normal conditions.

The pH of the oxidising composition is acid and may vary from 2 to 5, in particular from 2 to 4, and may be adjusted to the desired acid value by pH regulators which are well known in the art in the cosmetic treatment of keratin fibres, such as for instance phosphoric acid, ammonium phosphate, salicylic acid, etc.

According to the present invention, the oxidising composition comprises a first dye which per se assumes an azure or blue colour at a pH higher than 7 and optionally at least one second dye which per se assumes a red colour at a pH higher than 7.

In this context, it is essential for the choice of the aforesaid first dye and of the aforesaid second dye to fall within compounds having the above colour change features. These compounds must have enough chemical-physical stability both under acid pH conditions of the hydrogen peroxide-based oxidising composition and especially under strongly alkaline pH conditions that are determined at the time of use by mixing the hydrogen peroxide-based oxidising composition with a bleaching or dyeing composition (for instance oxidation dye) to form the emulsion to be applied to the hair.

Preferably, the first dye is chosen from the group consisting of the direct blue dye 3',3",5'5"-tetrabromophenolsulfonephtalein (bromophenol blue—CAS 115-39-9), the direct blue dye 3,3',3",4,5,5',5",6-ottabromophenol-sulfoneftalein (tetrabromophenol blue—CAS 4430-25-5) and combination thereof.

The amount of the first dye in the oxidising composition varies according to the desired blue/violet antireflection action and within the solubility limits of the first dye. Preferably, the content of the first dye (in particular bromophenol blue) is up to 1% by weight, more preferably from 0.1% to 0.3% of the weight of the oxidising composition.

Preferably, the second dye consists of the red pigment Acid Red 52 (C.I. 45100 CAS 3520-42-1—sulforodamine B sodium salt).

The amount of the second dye in the oxidising composition varies according to the needs and within the solubility limits of the second dye. Preferably, the content of the second dye (in particular acid red 52) is up to 5% by weight on the weight of the oxidising composition.

The oxidising composition may be obtained by dispersing the first dye and possibly the second dye, which are usually in the powder form, into the hydrogen peroxide aqueous solution so as to obtain a new solution or a cream having an acid pH lower than 7, for instance from 2 to 5 and preferably from 2 to 4 (optionally adjusted to said values with a pH regulator) and whose colour is generally variable from straw yellow to intense yellow.

Upon combination of the oxidising composition with the bleaching composition by the user when using the product according to the invention for hair bleaching, the alkaline strength of the bleaching composition prevails so much that the emulsion resulting from the combination stabilizes at a pH value higher than 7, generally between 8 and 11.5.

Therefore, if the oxidising composition only contains one or more dyes of the first type, namely dyes which per se assume an azure or blue colour at a pH higher than 7, upon combination of the oxidising composition with the bleaching composition a colour change of the aforesaid dye from yellow to blue/final blue is obtained. Said colour results to be chromatically active in the correction/elimination of the residual unaesthetic orange reflections on the hair due to previous treatments.

In this way, the above emulsion is effective in hair bleaching and, at the same time, advantageously, the azure/blue colour obtained results to be effective as a chromatic antagonist, thus eliminating the unaesthetic reflections present on the hair and resulting from the bleaching in yellowish, orange and/or reddish tones.

Vice versa, if the oxidising composition, in addition to containing dyes of the first type, also contains one or more dyes of the second type, namely dyes which per se assume a red colour at a pH higher than 7, upon combination of the oxidising composition with the bleaching composition a change in colour of both dyes of the above types from yellow to azure/blue and from yellow to red, respectively, is obtained and the resulting emulsion will have a purple colour.

In this way, the above emulsion is effective in hair bleaching and, at the same time, the purple colour thus obtained results to be advantageously active in an effective manner as a chromatic antagonist, thus eliminating the anaesthetic reflections present on the hair and deriving from the bleaching in the yellow, orange and/or red tones.

In the use of the bleaching product according to the invention, the mixing ratio between the bleaching composition and the oxidising composition may vary according to the needs. In particular, said mixing ratio may be comprised between 1:0.5 e 1:3, preferably the mixing ratio is 1:2.

As previously indicated, the present invention may also be applied to hair dyeing by means of oxidation dyes, in particular lightening and super-lightening dyes.

In this context, oxidation dye or permanent dye means any dye based on the oxidative transformation of colourless bases and on their polymerization with couplers. The permanent dye is indeed obtained through an oxidative process from non-coloured molecules, namely from colourless intermediates that become coloured and dyes through a dual oxidation and condensation process. Therefore, the oxidation dye contains an oxidation precursor and a coupler to give rise to the dyeing process and requires the presence of oxygenating agents such as hydrogen peroxide and of an alkaline environment, obtained for instance with addition of ammonia or monoethanolamine.

The oxidation precursor and the coupler may be usually selected from generally colourless or weakly coloured aromatic molecules, such as for instance paraphenylenediamine, metaminophenol, naphthenic and heterocyclic molecules. Exemplary molecules for the oxidation precursor and coupler include para-diaminobenzene, meta-diaminobenzene and p-aminophenol.

In the use for hair dyeing, the above described peroxide-based oxidising composition is combined with the oxidation dye according to a predefined mixing ratio, in particular a mixing ratio comprised between 1:0.5 e 1:3, preferably the mixing ratio is 1:1.5.

Upon combination of the oxidising composition with the oxidation dye by the user, the alkaline strength provided to an alkalizing agent (pH-regulator) present in the oxidising dye or added to the mixture (for instance ammonia/monoethanolamine) prevails and the emulsion resulting from the combination stabilizes at a pH value higher than 7, generally between 8 and 11.5.

Therefore, if the oxidising composition only contains one or more dyes of the first type, namely dyes which per se assume an azure or blue colour at a pH higher than 7, upon combination of the oxidising composition with the oxidation dye a change in colour of the above dye from yellow to azure/blue is obtained in the resulting emulsion to be applied to the hair.

In this way, the above emulsion is effective in hair dyeing and, at the same time, advantageously, the azure/blue colour obtained appears to be active in an effective manner as a chromatic antagonist, thus eliminating the anaesthetic reflections present on the hair and resulting from the treatment in the yellowish, orange and/or reddish tones.

Vice versa, if the oxidising composition in addition to containing dyes of the first type, also contains one or more dyes of the second type, namely dyes which per se assume a red colour at a pH higher than 7, upon combination of the oxidising composition with the oxidation dye a change in colour of both dyes of the above types from yellow to azure/blue and from yellow to red, respectively, is obtained and the resulting emulsion will have a purple colour.

In this way, the above emulsion is effective in hair dyeing and, at the same time, the purple colour thus obtained results to be advantageously active in an effective manner as a chromatic antagonist, thus eliminating the anaesthetic reflections present on the hair and resulting from the treatment in the yellowish, orange and/or reddish tones.

In light of the above, the present invention achieves the intended objects and a series of advantages compared to the currently used technique.

A first important advantage of the present invention lies in the fact that the pigment (or pigments) used to counteract the undesired reflections is more effectively dispersed or dissolved in the hydrogen peroxide oxidising solution compared to the bleaching composition, which results into a better activity and/or effectiveness thereof thanks to the fact that the pigment, since it is more effectively dispersed/solubilized, is able to better penetrate into the hair fibres and to better exercise the counteracting action of the unwanted reflections.

Another advantage of the present invention lies in the fact that the formation of the emulsion by mixing the bleaching composition in oil with the hydrogen peroxide-based oxidising composition and the subsequent application thereof to the hair appears to be easier and more comfortable because the resulting emulsion does not drip, although derived from two liquid products, when applied to the hair.

A further important advantage of the present invention is represented by the wide applicability of the oxidising composition containing hydrogen peroxide and the pigment (or pigments) for the action of counteracting unwanted reflections by means of a chromatic combination, not only in hair bleaching but also in hair dyeing, lightening and super-lightening products.

Indeed, the oxidising composition according to the invention containing hydrogen peroxide and pigment (or pigments) for the action of counteracting unwanted reflections by means of a chromatic combination may be effectively applied in combination at least with 1) bleaching cream, 2) bleaching oil, 3) bleaching paste, 4) bleaching powder, 5) lightening dyes, 6) super-lightening dyes and 7) oxidation dyes.

A skilled person may make several changes and variants to the oxidising composition according to the invention in order to meet specific and contingent needs, which however are all comprised within the scope of protection of the appended claims.

The invention claimed is:

1. Peroxide-based oxidising composition for use in hair bleaching or with oxidation dyes, the composition consisting of, in a cosmetically acceptable carrier, hydrogen peroxide in proportions from 1% to 12% by weight on the weight of the composition, at least one first dye which per se assumes an azure or blue colour at a pH higher than 7 and at least one second dye which per se assumes a red colour at a pH higher than 7.

2. Oxidising composition according to claim 1, wherein the cosmetically acceptable carrier is water and the hydrogen peroxide is an aqueous solution of hydrogen peroxide in proportions from 1% to 12% by weight on the weight of the composition.

3. Oxidising composition according to claim 1, wherein the at least one first dye is chosen from the group consisting of the direct blue dye 3',3",5'5"-tetrabromophenolsulfonephtalein (bromophenol blue—CAS 115-39-9), the direct blue dye 3,3',3",4,5,5',5",6-ottabromophenol-sulfoneftalein (tetrabromophenol blue—CAS 4430-25-5) and combination thereof.

4. Oxidising composition according to claim 3, wherein the amount of the at least one first dye is up to 1% by weight on the weight of the oxidising composition.

5. Oxidising composition according to claim 4, wherein the amount of the at least one first dye is from 0.1% to 0.3% by weight on the weight of the oxidising composition.

6. Oxidising composition according to claim 1, wherein the at least one second dye consists of the red pigment Acid Red 52 (C.I. 45100 CAS 3520-42-1-sulforodamine B sodium salt).

7. Oxidising composition according to claim 6, wherein the at least one second dye is up to 5% by weight on the weight of the oxidising composition.

8. A kit for hair bleaching comprising, in separate containers:
 a) an oxidising composition according to claim 1,
 b) a bleaching composition containing an oxidising agent other than hydrogen peroxide and at least one pH-adjusting agent able to change the pH to a value higher than 7, when the oxidising composition is mixed with the bleaching composition.

9. Kit according to claim 8, wherein the oxidising agent is selected from the group consisting of potassium persulfate, sodium persulfate, ammonium persulfate and mixtures thereof and the at least one pH-adjusting agent is selected from the group consisting of sodium metasilicate, silicate compounds and carbonate compounds.

10. A kit for hair dyeing comprising in separate containers:
 a) an oxidising composition according to claim 1,
 b) an oxidation dye comprising an oxidation precursor and a coupler,
 c) at least one pH-adjusting agent present in the oxidation dye or separately able to change the pH to a value higher than 7, when the oxidising composition is mixed with the oxidation dye and the at least one pH-adjusting agent.

11. Peroxide-based oxidising composition for use in hair bleaching or with oxidation dyes, the composition consisting of water, hydrogen peroxide in proportions from 1% to 12% by weight on the weight of the composition, up to 1% by weight on the weight of the composition of a first dye which per se assumes an azure or blue colour at a pH higher than 7 and up to 5% by weight on the weight of the oxidising composition of at least one second dye which per se assumes a red colour at a pH higher than 7, wherein
 the first dye is the direct blue dye 3',3",5'5"-tetrabromophenolsulfonephtalein (bromophenol blue—CAS 115-39-9), the direct blue dye 3,3',3",4,5,5',5",6-ottabromophenol-sulfoneftalein (tetrabromophenol blue—CAS 4430-25-5) or a combination thereof, and
 the at least one second dye is red pigment Acid Red 52 (C.I. 45100 CAS 3520-42-1-sulforodamine B sodium salt).

12. Method of bleaching or dyeing-hair, said method comprising:
 preparing a peroxide-based oxidizing composition consisting of
 hydrogen peroxide,
 at least one first dye which per se assumes an azure or blue colour at a pH higher than 7,
 a cosmetically acceptable carrier, and
 at least one second dye which per se assumes a red colour at a pH higher than 7, wherein said hydrogen peroxide is in proportions from 1% to 12% by weight on the weight of the composition,
 mixing the peroxide-based oxidizing composition with a bleaching composition containing an oxidizing agent other than hydrogen peroxide and at least one pH-adjusting agent able to change the pH to a value higher than 7 when the peroxide-based oxidizing composition is mixed with the bleaching composition thereby obtaining an emulsion; or
 mixing the peroxide-based oxidizing composition with an oxidation dye comprising an oxidation precursor and a coupler and with at least one pH-adjusting agent present in the oxidation dye or separately able to change the pH to a value higher than 7 when the peroxide-based oxidizing composition is mixed with the oxidation dye and the at least one pH-adjusting agent, thereby obtaining an emulsion; and applying the emulsion to the hair.

13. The method according to claim 12, wherein the mixing ratio between the bleaching composition and the peroxide-based oxidizing composition is comprised between 1:0.5 and 1:3.

14. The method according to claim 12, wherein the mixing ratio between the peroxide-based oxidizing composition and the oxidation dye is comprised between 1:0.5 and 1:3.

* * * * *